United States Patent
Wang et al.

(10) Patent No.: US 7,524,277 B1
(45) Date of Patent: Apr. 28, 2009

(54) APEX TO AORTA CANNULA ASSEMBLY

(75) Inventors: Dongfang Wang, Galveston, TX (US); Joseph B. Zwischenberger, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 415 days.

(21) Appl. No.: 11/055,236

(22) Filed: Feb. 10, 2005

Related U.S. Application Data

(60) Provisional application No. 60/543,799, filed on Feb. 11, 2004.

(51) Int. Cl.
 *A61M 1/10* (2006.01)
(52) U.S. Cl. .................... 600/16; 623/3.13; 623/3.15
(58) Field of Classification Search .............. 623/3.13, 623/3.15; 600/160, 16
 See application file for complete search history.

(56) References Cited

U.S. PATENT DOCUMENTS

| | | | | |
|---|---|---|---|---|
| 2,652,831 | A * | 9/1953 | Chesler ..................... 422/47 |
| 4,565,544 | A * | 1/1986 | Muller et al. ............ 604/164.04 |
| 5,376,114 | A | 12/1994 | Jarvik |
| 5,776,190 | A * | 7/1998 | Jarvik ........................ 600/16 |
| 5,824,070 | A | 10/1998 | Jarvik |
| 5,851,174 | A * | 12/1998 | Jarvik et al. ................. 600/16 |
| 5,888,241 | A | 3/1999 | Jarvik |
| 6,210,363 | B1 * | 4/2001 | Esch et al. ............... 604/96.01 |
| 6,537,315 | B2 * | 3/2003 | Yamazaki et al. .......... 623/3.13 |
| 6,716,189 | B1 | 4/2004 | Jarvik et al. |
| 2002/0177822 | A1 * | 11/2002 | St. Cyr et al. ............... 604/264 |

OTHER PUBLICATIONS

Norman J.C., A Single Cannula for Aoritc Perfusion and Left Ventricular Decompression, Oct. 1970, Chest, vol. 58 No. 4, pp. 378-379, accessed at www.chestjournal.org on Jul. 30, 2007.*

Zink, M., et al., "Successful temporary left ventricular assistance with the hemopump assist device during acute myocardial infarction after complex mitral valve surgery," Intensive Care Med. Nov. 2000;26(11):1710. No Abstract available.

(Continued)

*Primary Examiner*—Carl H Layno
*Assistant Examiner*—Jennifer Stewart
(74) *Attorney, Agent, or Firm*—Locke Lord Bissell & Liddell LLP

(57) ABSTRACT

An apparatus, system, and method for assisting a heart in circulating blood that has been damaged, for example, by a myocardial infarction. In at least one aspect, an apparatus, system, and method are used for inserting a single cannula assembly comprising at least an inner and outer cannula into the left ventricle, advancing the inner cannula portion of the cannula assembly past the aortic valve, and into the aorta without requiring a secondary cannula insertion through an external portion of the aorta. In another aspect, an intraventricular assistant device (IVAD) having a motor and impeller can be inserted directly into the heart, such as in the left ventricle. The IVAD uniquely provides a pump within the heart through a single insertion that can reduce thrombosis and lessen the complexities typically associated with such efforts.

18 Claims, 4 Drawing Sheets

OTHER PUBLICATIONS

Sweeney, M.S., "The Hemopump in 1997: a clinical, political, and marketing evolution," Ann Thorac Surg. Aug. 1999;68(2):761-3, PMID: 0475484 [PubMed—indexed for MEDLINE].

Lachat, M, et al., "Hemodynamic properties of the hemopump," HP14.Int J Artif Organs. Mar. 1999;22(3):155-9.

Scholtz, K.H., et al., "Clinical experience with the percutaneous hemopump during high-risk coronary angioplasty," Am J Cardiol. Nov. 1, 1998;82(9):1107-10, A6.

Isogro, F., et al., "Intracardiac left ventricular support in beating heart, multi-vessel revascularization.,"J. Card Surg. May-Jun. 2003;18(3):240-4.

Meyns, B., et al., "Left ventricular support by catheter-mounted axial flow pump reduces infarct size," J Am Coll Cardiol. Apr. 2, 2003;41(7):1087-95.

Vercaemst, L., et al., "A miniaturized cardiac support system in an era of minimal invasive cardiac surgery," J Extra Corpor Technol. Jun. 2002;34(2):92-100.

Dreyfus M.D., G.D., "Hemopump 31, the Sternotomy Hemopump: Clinical Experience," The Society of Thoracic Surgeons, 1996.

Lonn, M.D., Ph.D., U., et al., "Beating heart coronory surgery supported by an axial blood flow pump" The Society of Thoracic Surgeons, 1996.

Song, X, et al., "Axial flow blood pumps," American Society of Artificial Internal Organs Journal, 2003.

* cited by examiner

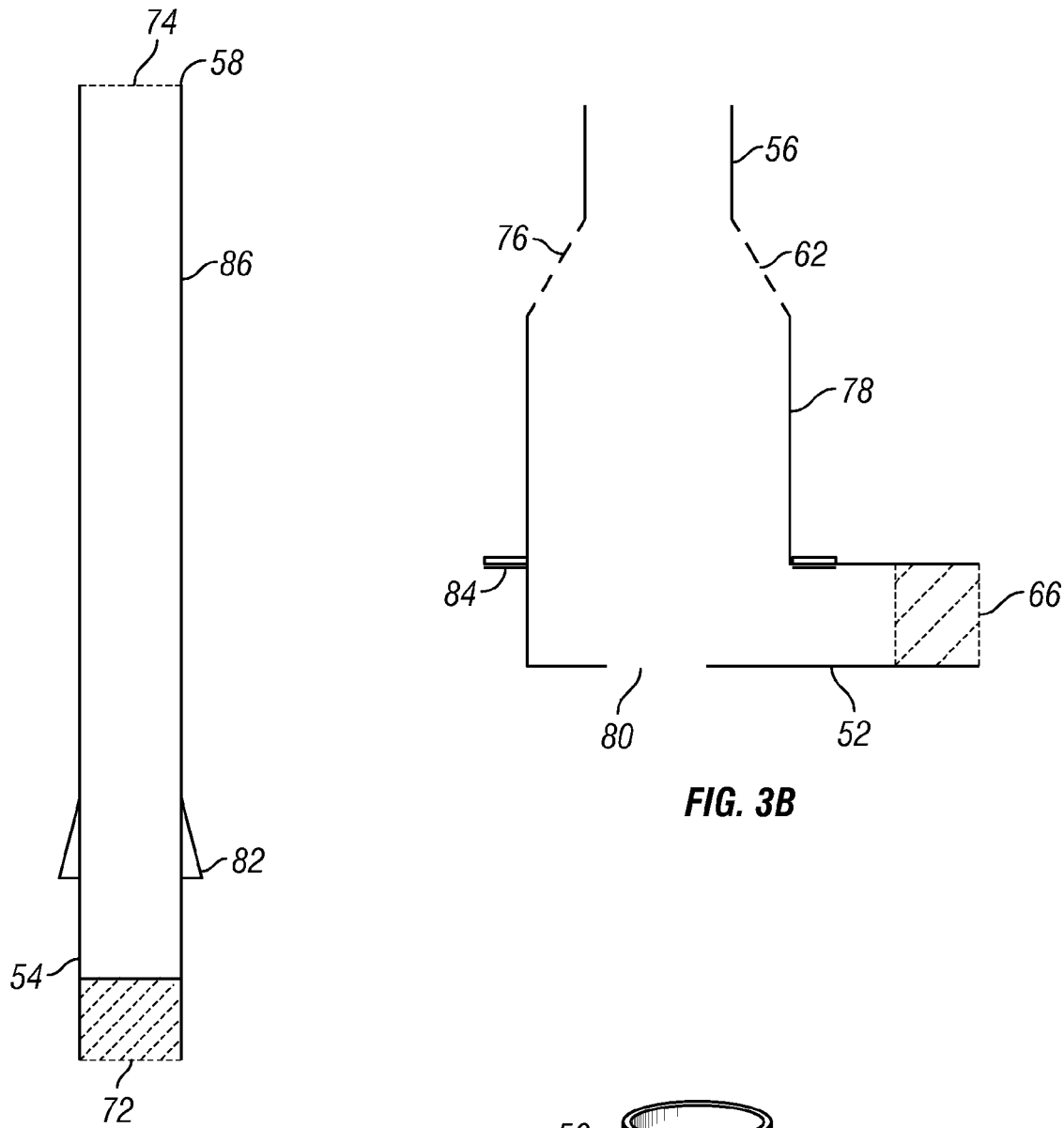
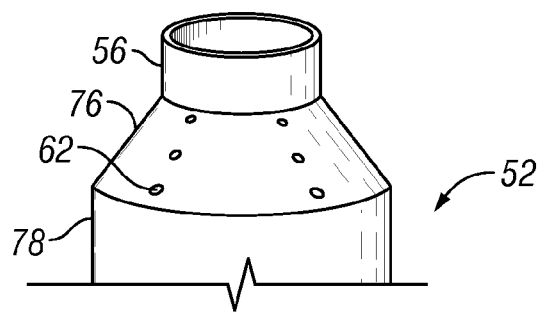
FIG. 3A
FIG. 3B
FIG. 3C

APEX TO AORTA CANNULA ASSEMBLY

This application claims the benefit of U.S. Provisional Application Ser. No. 60/543,799, filed Feb. 11, 2004.

FIELD OF THE INVENTION

The invention relates to the field of medical devices. More specifically, the invention relates to the design and use of cardiac medical devices.

BACKGROUND OF THE INVENTION

Tissue decay in a heart typically results from a myocardial infarction (MI). Often, the decay results in chronic heart degradation and ultimate failure, as the damaged portion is unable to be restored. The deterioration is especially acute when the damage occurs to the left ventricle, which functions at a high pressure during systolic contractions to pump the blood received from the left atrium and the mitral valve, through the aortic valve and into the aorta for distribution throughout the body. The damaged tissue, operating under high pressures, eventually fails. Even without a failure, the heart is unable to function at a performance level prior to the MI, resulting in less circulation and lower blood oxygen levels.

Although cutting edge, critical care technology has been applied in the treatment and restoration of the cardiac tissues after an MI, the typical procedures are traumatic to many patients and sometimes result in mortality. Less tissue decay can result from immediate and efficient cardiac or combined cardiac and pulmonary support, but the current technology is lacking in both aspects. Current technology, including a left ventricle assist device (LVAD), extracorporeal membrane oxygenation (ECMO), and cardiopulmonary support (CPS), is either less efficient or too complicated and traumatic to already impaired anatomical systems.

Veno-Arterial (V-A) ECMO with peripheral arterial venous access using percutaneous cannulae has been available for cardiopulmonary support for several decades. Typically, a cannula is inserted into a vena cava, blood is routed through the cannula to an ECMO system for oxygenation, and the blood is returned to an artery. The multiple insertions causes trauma, can result in bleeding especially by the return path to the arterial system, and the flow rates are limited by high resistance. ECMO is also time limited, generally to less than four weeks, and has been shown to induce damage to the red blood cell (RBC). Further, ECMO does not unload the left ventricle, resulting in contractions and continued stress on the cardiac tissues. Thus, the left ventricle is unable to relax to allow at least partial healing of the muscle tissues by, for example, new growth.

LVAD systems have been used for longer-term, left ventricular support and reduced damage to the RBC. The LVAD removes blood flowing into the left ventricle, so that the left ventricle contracts at a significantly lower pressure in a more relaxed state. The blood flows to the LVAD pump and is pumped back into the aorta at an increased pressure to reduce the load on the left ventricle. However, current technology typically requires LVAD systems to be inserted into both the left ventricle to remove the blood and then returned to the aorta by a separate anastomosis of another cannula. The outlet cannula anastomosed to the aorta can especially cause complications because of the no-flow segment of the aorta root below the anastomosis, and has the possibility of clotting, thrombosis, and strokes.

Some efforts have resulted in a pump routed to the left ventricle by inserting a cable attached to an impeller into a location below the iliac artery and routing the impeller back up into the aorta, back through the aortic valve and into the left ventricle. The motor is typically located external to the body or at least the artery. The motor rotates the cable, which in turn rotates the impeller to supplement the pumping of the left ventricle. The cable, the arterial insertion, and the impeller can cause physical damage and thrombosis.

An insertion from the apex of the heart directly to the aorta was proposed about three decades ago, but the complexities of insertion and advancement to the aorta proved to be unfeasible in practice and thus did not enable the concept. Further, the cannula was not able to penetrate the chest wall and subsequently connect to a paracorporeal blood pump and oxygenator.

Even if the above procedures result in no adverse consequences, they are often performed at a subsequent time, when damage to the heart has largely occurred, due to their complexity. Further, the procedures are expensive and unavailable to many persons in need. The prognosis for healing after an MI can be greatly affected by the efficiency and availability of providing rapid assistance to the heart to encourage its healing and to provide oxygenation and circulation to supply blood to the anatomy.

Therefore, there remains a need for a simple, relatively easily accessible system and method for rapid provision of assistive devices for cardiac and/or pulmonary support.

SUMMARY OF THE INVENTION

The present invention provides an apparatus, system, and method for assisting a heart in circulating blood that has been damaged, for example, by a myocardial infarction. In at least one aspect, the invention provides an apparatus, system, and method for inserting a single cannula assembly comprising at least an inner and outer cannula into the left ventricle, advancing the inner cannula of the cannula assembly past the aortic valve, and into the aorta without requiring a secondary cannula incision through an external portion of the aorta. Certain shapes and flow paths reduce thrombosis and help ensure sealing into the apex and through the aortic valve. Blood entering the left ventricle through the mitral valve is withdrawn at a sufficient rate to allow the left ventricle to either not contract or to contract at a sufficient low pressure that can help the damaged area in restoration.

In another aspect, the invention provides an intraventricular assistant device (IVAD) having a motor and impeller that can be inserted directly into the heart, such as in the left ventricle. The IVAD uniquely provides a pump within the heart through a single insertion that can reduce thrombosis and lessen the complexities typically associated with such efforts The disclosure provides a method of withdrawing blood from a heart of a body, the heart having an apex in proximity to a left ventricle and an aortic valve fluidicly disposed between the left ventricle and an aorta, the aorta providing a distribution of blood to the body, comprising: obtaining a cannula assembly having a first cannula and a second cannula; creating an incision in proximity of the apex of the heart; inserting the cannula assembly through the incision and into the left ventricle of the heart, the first cannula being disposed in the left ventricle and fluidicly coupled to the left ventricle; inserting a portion of the second cannula through the aortic valve of the heart; and allowing blood to be withdrawn from the left ventricle through the first cannula separate from a blood flow through the second cannula.

The disclosure further provides a system for withdrawing blood from a heart of a body, the heart having an apex in proximity to a left ventricle and an aortic valve fluidicly disposed between the left ventricle and an aorta, the aorta providing a distribution of blood to the body, comprising: a cannula assembly having an outer cannula and an inner cannula, comprising: the inner cannula having an outer perimeter disposed inside an inner perimeter of the outer cannula, and having a tapered tip adapted to be introduced through the heart apex and extended through the aortic valve; and the outer cannula having a transition portion having a first introductory inner perimeter disposed toward a portion of the cannula assembly adapted to be introduced through an incision in the apex of the heart, the introductory inner perimeter being sized in proximity to an outer perimeter of the inner cannula to reduce blood flow therebetween, the transition portion further having a second inner perimeter larger than the first introductory perimeter and distal from the portion to be introduced through the incision, the outer cannula forming an annulus around the inner cannula fluidicly separate from the inner cannula, the outer cannula having at least one port to allow blood to be withdrawn from the left ventricle to flow through the annulus to an outlet of the outer cannula.

The disclosure further provides a method of circulating blood in a heart of a body, the heart having an apex in proximity to a left ventricle and an aortic valve fluidicly disposed between the left ventricle and an aorta, the aorta providing a distribution of blood to the body, comprising: obtaining an intraventricular device, having a cannula and a pump coupled to the cannula, the pump having an inlet and an outlet; creating an incision in proximity of the apex of the heart; inserting the intraventricular device at least partially through the incision and into the left ventricle of the heart to fluidicly couple the pump inlet to the left ventricle; inserting a portion of the cannula through the aortic valve of the heart to fluidicly couple the pump outlet to the aorta; and allowing blood to be withdrawn from the left ventricle into the inlet of the pump in the left ventricle.

The disclosure also provides a system of circulating blood in a heart of a body, the heart having an apex in proximity to a left ventricle and an aortic valve fluidicly disposed between the left ventricle and an aorta, the aorta providing a distribution of blood to the body, comprising an intraventricular device, comprising: a cannula adapted to be inserted into the left ventricle through an incision in the heart and a portion of the cannula adapted to be inserted through the aortic valve using the same incision; and a pump coupled to the cannula, the pump having an inlet and an outlet, the pump being adapted to be at least partially inserted into the left ventricle with the cannula, the inlet being fluidicly coupled to the left ventricle and the outlet being fluidicly coupled to the aorta.

BRIEF DESCRIPTION OF THE DRAWINGS

A more particular description of the invention, briefly summarized above, may be had by reference to the embodiments thereof which are illustrated in the appended drawings and described herein. It is to be noted, however, that the appended drawings illustrate only some embodiments of the invention and are therefore not to be considered limiting of its scope, because the invention may admit to other equally effective embodiments.

FIG. 3A illustrates a cross sectional schematic of an inner cannula.

FIG. 3B illustrates a cross sectional schematic of an outer cannula.

FIG. 3C illustrates a cross sectional schematic of an upper portion of the outer cannula.

DETAILED DESCRIPTION OF A PREFERRED EMBODIMENT

In general, the invention provides a cannula assembly having a double wall to create a readily installed, high-flow, low-resistant apex-to-aorta shunt that allows for rapid attachment to a blood-pumping device such as a ventricular assistant device, or a combination ventricular assistant device/oxygenator. The procedure for placement of the present invention cannula assembly is generally relatively simple, less time consuming, and less invasive than previous methods. In another aspect, the present invention provides a single lumen cannula with a built-in intraventricular pump that can be inserted at the apex of the heart and pumps blood from the left ventricle across the aortic valve to the ascending aorta.

Figure 1:
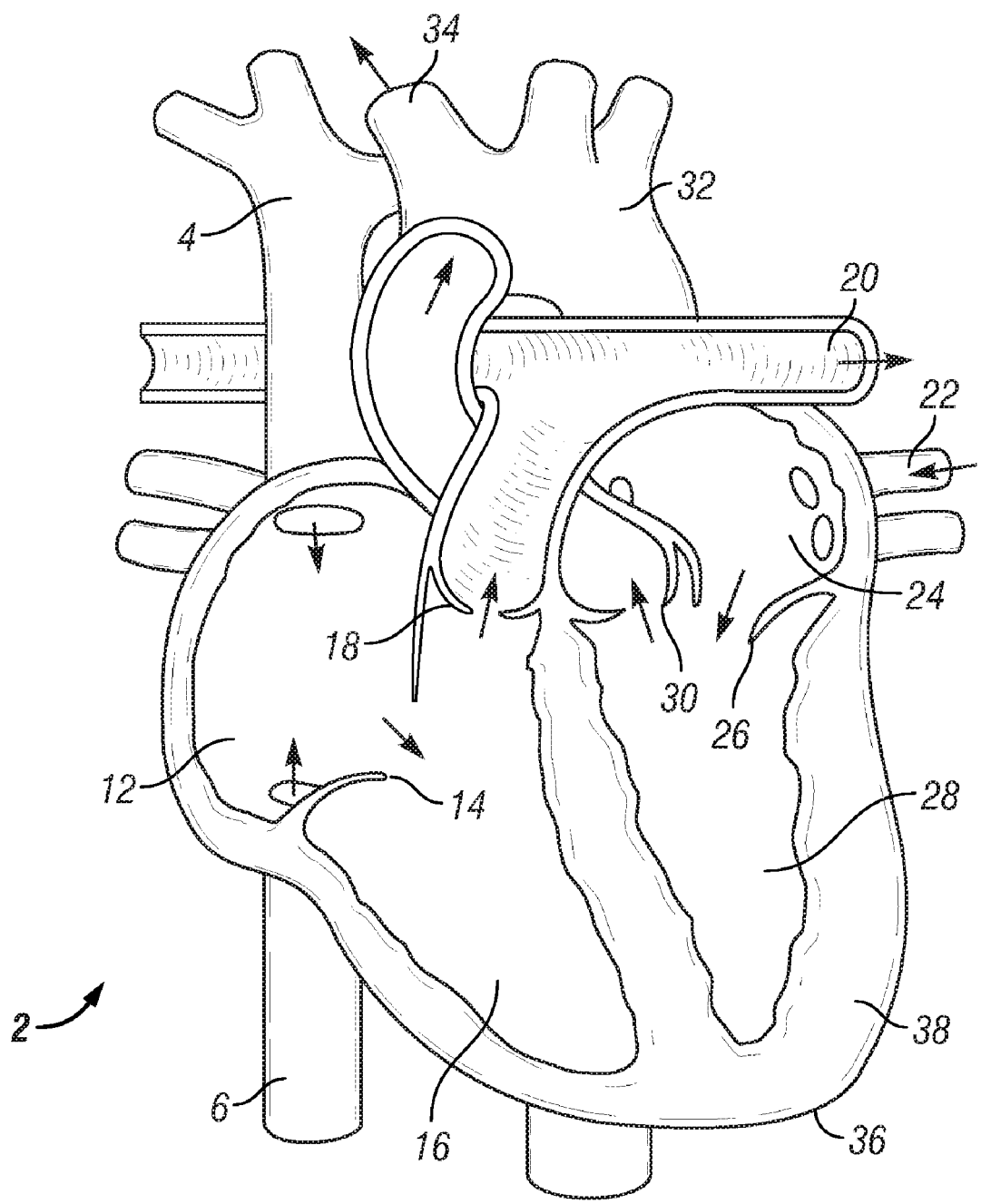
FIG. 1 is a diagram of a heart showing the various portions relevant to the present invention.

FIG. 1 is a diagram of a heart showing various portions relevant to the present invention. The following brief summary of the heart's circulatory system is included to provide a better understanding of the present invention. In general, a heart 2 receives blood from veins, pumps the oxygenated blood through the lungs, where the blood is returned to the heart as oxygenated blood. The heart then pumps the oxygenated blood through the aorta to the various arteries throughout the body. More specifically, the heart 2 receives blood from the superior vena cava 4 and the inferior vena cava 6 into the right atrium 12. The right atrium 12 then contracts to force the blood through the tricuspid valve 14 into the right ventricle 16. The right ventricle 16 contracts at a relatively small contraction pressure to force the blood through the pulmonary valve 18 into the pulmonary artery 20. The pulmonary artery 20 directs blood to the lungs (not shown) where the blood is oxygenated. From the lungs, the oxygenated blood is returned to the heart 2 through pulmonary vein 22 into the left atrium 24. The left atrium 24, again operating a low pressure, such as less than 18 mm of mercury, pushes the blood through the mitral valve 26 into the left ventricle 28. The left ventricle 28 provides the main pumping chamber for the heart at a higher pressure of approximately 100 mm of mercury. The blood pumped from the left ventricle exits through the aortic valve 30 into the aorta 32 in the lower region known as the aortic root. The aorta 32 then acts as a distribution chamber for the various greater arteries 34.

Acute heart failure can occur in either ventricle, but generally is more problematic in the left ventricle, because the left ventricle provides the primary pressure to the artery system of the body. Sometimes, the tissues of the heart can at least partially be restored by draining the blood supply, or "unloading", from the particular ventricle, so that the contraction pressure is minimized. Generally, when a patient is undergoing heart surgery, the heart is by-passed by taking blood from the vena cava, pumping it through an extracorporeal oxygenator, and then returned via an arterial cannula into the root of the ascending aorta emanating from the aortic arch. Additional methods may employ cannulating through the outer heart tissue 38 in the vicinity of a lower portion of the heart, known as the apex 36, and unloading the heart thusly. As described in the background, some systems unload the blood from the left ventricle, circulate to an extracorporeal pump and recirculate it to yet another cannula inserted through the wall of the aorta with the problems described above.

A. Apex-to-Aorta Cannula Assembly

Figure 2:
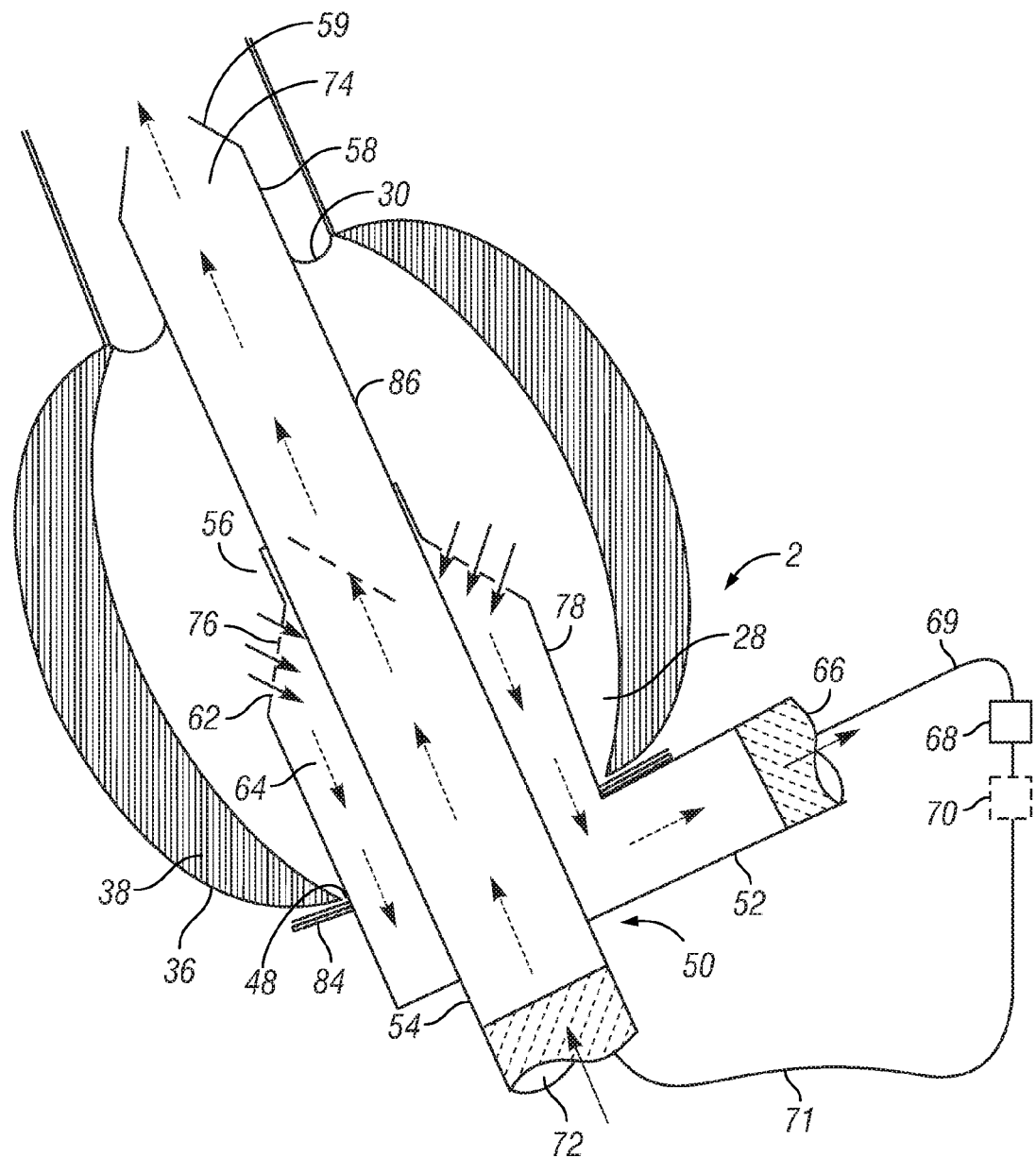
FIG. 2 is a diagram of a cannula assembly that can be inserted through the apex into the left ventricle and through the aortic valve directly into the aorta root.

FIG. 2 is a diagram of a cannula assembly that can be inserted through the apex into the left ventricle and through the aortic valve directly into the aorta. In general, the insertion is made through a single incision without the need for another cannula inserted through the aorta wall. The present invention provides a cannula assembly 50 that generally includes two primary components to form a double wall cannula assembly: an outer cannula 52 and an inner cannula 54 coupled to the outer cannula. In at least one embodiment, the inner cannula is slidably coupled to the outer cannula.

The outer cannula 52 includes a larger portion 78 that is larger than the inner cannula 54 to form an annulus 64 therebetween. An upper portion of the outer cannula 52 forms a lumen 56. The lumen 56 is sized to fit closely to an upper portion of the inner cannula 54. The inner cannula forms a lumen 86 as a blood flow path for returning the blood to the body through the aortic valve into the aorta as described herein. The inner cannula 54 includes a portion herein termed a tip 58 that is sufficiently long to be inserted through the aortic valve 30 above the left ventricle 28 toward the aorta. A transition portion is formed in the outer cannula 52 between the lumen 56 and the larger portion 78. In one embodiment, the transition portion can be a cone 76. The cone 76 includes one or more ports 62 that are fluidicly coupled to the annulus 64. Other locations of the ports 62 can be formed in the outer cannula 52. For example, one or more ports 62 can be located toward a lower portion of the outer cannula to provide the ability to withdraw blood from a position closer to the apex 36. Alternatively, the ports 62 in the cone 76 or at other locations can be located closer to the apex 36 by locating the outer cannula 52 at a different position relative to the heart 2 and the apex 36. Further, ports can also be formed in the tip 58 above the aortic valve 30. In general, the blood flow path is generally designed to reduce stagnant areas of blood flow and lower the risk of thrombosis.

The outer cannula 52 includes an outlet 66 that is coupled to a tubing 69. The outlet can form a "tail" portion as a side outlet, with the understanding that various angles can be used without limitation. The tubing 69 can be coupled to a pump 68 and an optional oxygenator 70. The outlet of the pump 68 (and/or oxygenator 70) is coupled to a return tubing 71. The return tubing 71 is coupled to an inlet 72 of the inner cannula 54.

A securing plate 84 can be coupled to the outer cannula 52. The securing plate can be used to suture the cannula assembly 50 to heart to maintain a fixed location of the cannula assembly.

In operation, a small incision 48 is made in the region of the apex 36 through the heart tissue 38 of the heart 2. The outer cannula lumen 56 is inserted into the incision 48. The transition piece, such as the cone 76, can then expand the incision 48 to allow the larger portion 78 of the cannula assembly to be inserted into the left ventricle. The lumen 86 of the inner cannula 54 can be slidably coupled with the outer cannula 52, so that the tip 58 can be advanced through the left ventricle cavity and through the aortic valve 30. The tip 58 can include an introducer 59 to assist in smoothly engaging the aortic valve 30. The outlet 56 of the outer cannula 52 can be coupled to the pump 68 and possibly an oxygenator 70, where one or both of the instruments can be located percutaneously or extracorporeally.

In another embodiment, the inner cannula 54 can already be position in an extended mode in the outer cannula 52 and sealingly coupled to the outer cannula 52. Thus, upon insertion of the cannula assembly 50 through the incision 48, the tip 58, and any introducer 59 included therewith, first enters the incision 48 followed by the lumen 56, the cone 76, and the larger portion 78. As the outer cannula is advanced and then seated, the inner cannula 54 is also advanced through the aortic valve 30 into the aorta.

Blood entering the left ventricle 28 readily flows into the annulus 64 through the ports 62 of the outer cannula 52 separate from flow through the inner cannula. The blood then flows out of the cannula outlet 66 through the tubing 69, pump 68, optional oxygenator 70, tubing 71, and into the inlet 72 of the inner cannula 54. The blood then flows directly through the aortic valve 30 into the aorta (not shown) through the outlet 74 of the inner cannula 54.

The incision 48 in the left ventricle is generally aligned with the aortic valve 30 so that the lumen 86 can be readily inserted therethrough. This incision is in an area of the heart 2 that is generally used to unload from the left ventricle during cardiac surgery. Thus, it is believed that many physicians will readily adapt to the disclosed concept upon understanding the present invention. The readily available placement of the cannula assembly can reduce cost in providing assistant devices as well as provide less trauma to the patient by providing a single insertion, because the cannula assembly can extract and inject blood through only one incision. It is believed that the location of the single insertion, coupled with the unloading of the left ventricle, allows for the left ventricle to either not contract at all or to contract at a much lower contraction pressure that reduces ischemia or circulatory instability. Further, the more relaxed state of the left ventricle will allow it to more readily restore with time if indeed restoration is possible. Still further, an external cannula assembly, typical with prior art, is unnecessary with the present invention. Thus, the risk of post-operative thrombosis and need for corrective surgery due to post-operative bleeding is reduced.

FIGS. 3A-3C illustrate various details of the inner cannula and outer cannula in disassembled form for at least one embodiment.

FIG. 3A illustrates a cross sectional schematic of the inner cannula. The inner cannula 54 forms a lumen 86 having an inlet 72 and an outlet 74. A circumferential seal 82, such as a seal formed of silicone or other sealing material known to those with ordinary skill in the art, is disposed on the inner cannula 54, on the outer cannula 52, or both. The seal 82 is used to sealingly engage an opening in the outer cannula 52 described herein. An introducer 59, shown in FIG. 2, can be coupled to the tip 58 of the inner cannula 54 to assist in engaging the aortic valve 30, and potentially the incision 48, if inserted first.

FIG. 3B illustrates a cross sectional schematic of the outer cannula. The outer cannula 52 includes a lumen 56 sized to approximate the outer periphery of the inner cannula 54. The relative close dimensions can reduce blood flow therebetween. A transition piece, such as cone 76, can transition from the cross-sectional area of the lumen 56 to a larger portion 78 of the outer cannula 52. In at least one embodiment, the cone 76 includes one or more ports 62 through which the blood can enter the outer cannula 52. An outlet 66 is fluidicly disposed opposite the port 62 and the lumen 56. The outer cannula 52 also includes an opening 80 sized to accept the inner cannula 54 and to form a seal therewith in conjunction with the seal 82 when assembled.

The outer cannula 52 can also include a securing plate 84. The securing plate 84 can be used to secure the cannula assembly 50 to the cardiac tissues, such as shown in FIG. 2.

FIG. 3C illustrates a cross sectional schematic of an upper portion of the outer cannula 52. The outer cannula 52 includes the lumen 56, a transition cone 76 having one or more ports 62 that is coupled to a larger portion 78. Further, the angle of the transition piece and its associated length can vary in accordance with the desired flow rates, and flow locations, to avoid thrombosis and other deteriorating factors. The number of ports 62 can vary depending on the particular application, the rate of flow, size of an annulus between the outer cannula 52 and inner cannula 54, and other factors. Further, various physiological factors can be considered in sizing the ports, annulus, as well as the pump, tubing sizes, outlets, and other flow channels. Such factors include without limitation, the avoidance or reduction of hemolysis, that is, the destruction of the red corpuscles due to disadvantageous flow rates. Flow should be sufficient so as to induce high shear forces at the surfaces, yet not create turbulence or vortices that will occasion clotting and thrombus formation. Flows are generally in the 3-5 liters/min. range, although other flow rates are possible.

FIGS. 4A-4E will be described in conjunction with one another, and are included to show various cross-sectional details of the cannula assembly.

Figure 4B:
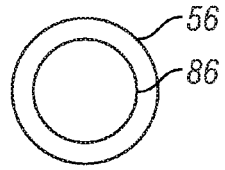
FIG. 4B illustrates a cross sectional schematic at an interface of the outer cannula and inner cannula.
Figure 4C:
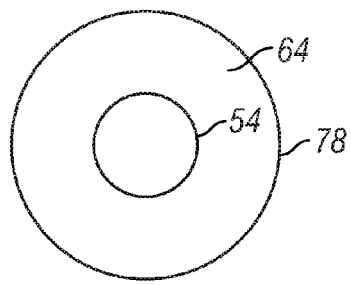
FIG. 4C illustrates a cross sectional schematic of the flow area between the outer cannula and the inner cannula.
Figure 4D:
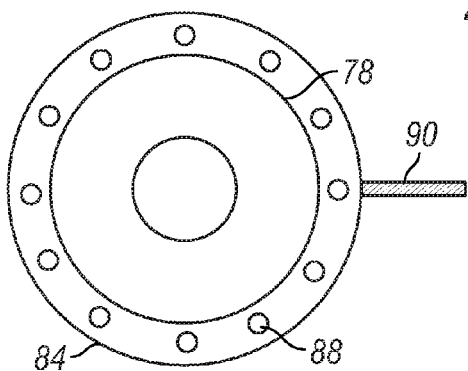
FIG. 4D illustrates a cross sectional schematic of a securing plate coupled to the outer cannula.
Figure 4A:
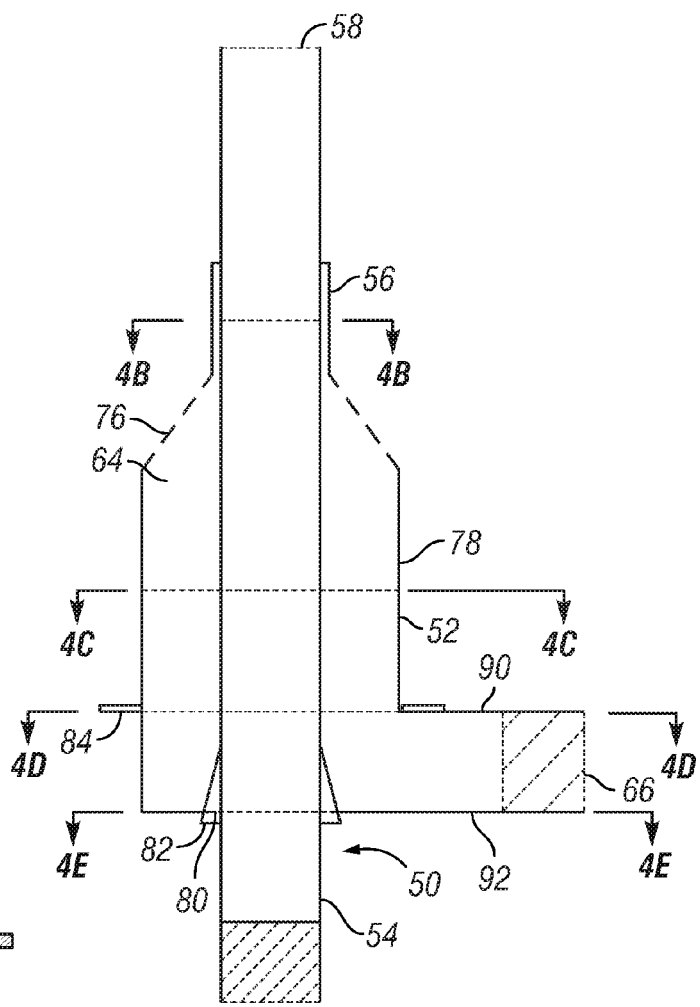
FIG. 4A illustrates the cannula assembly in an assembled condition.

FIG. 4A illustrates the cannula assembly in an assembled state. The cannula assembly 50 includes the outer cannula 52 and the inner cannula 54. In at least one embodiment, the inner cannula 54 is assembled with the outer cannula 52 through an opening 80. The opening 80 can be sealed with a seal 82. The seal 82 is disposed around the periphery of the inner cannula 54, or alternatively, around the opening 80, or a combination thereof. In at least one embodiment, the seal 82 can be formed at an angle to form a transitional sealing surface. If a surgeon wishes to advance the inner cannula 54 into the aortic valve shown in FIG. 2, after the insertion of the outer cannula 52 in the ventricle, then the seal 82 can be advanced into a sealing position upon proper placement of the inner cannula 54. A securing plate 84 can be coupled at some location on the outer cannula 52 to help attach the cannula assembly 50 to the cardiac tissues. Further, an upper portion 90 of the outlet of the outer cannula 52 can be coupled with a lower portion 92 of the outlet of the outer cannula 52 for manufacturing convenience. The upper portion 90 coupled with the lower portion 92 can form an outlet 66 in the shape of a "tail" of the outer cannula to assist in coupled the tubing 69 thereto. In at least one embodiment, the tail can extend in a sideways direction from the longitudinal axis of the inner cannula, although other angles can be used. Alternatively, the outlet 66 can be formed and attached to the outer cannula by forming an opening in the side of the larger portion 78 and sealingly coupling the tail thereto.

FIG. 4B illustrates a cross sectional schematic at an interface of the outer cannula and inner cannula. The lumen 56 on the outer cannula 52 is shown in close proximity to the outer periphery of the inner cannula 54. The close proximity minimizes blood flow by-pass between the lumen 56 and the inner cannula 54.

FIG. 4C illustrates a cross sectional schematic of the flow area between the outer cannula and the inner cannula. The change in relative cross sections is shown between the inner periphery of the larger portion 78 of the outer cannula 52 compared to the outer periphery of the inner cannula 54 to create the annulus 64. The annulus 64 is generally sized to permit high blood flow with low resistance. This sizing can help protect red blood cells from hemolysis.

FIG. 4D illustrates a cross sectional schematic of a securing plate coupled to the outer cannula. The securing plate 84 is generally coupled to an outer periphery of the larger portion 78 of the outer cannula 52. The securing plate 84 can include one or more suture holes 88 that allow a surgeon to couple the securing plate and associated cannula assembly 50 to tissue, such as cardiac tissue. A top portion 90 of the outer cannula 52 outlet is also shown in FIG. 4D. The tail forming the outer cannula outlet 66 can have a variety of shapes as is customary to the art. In other embodiments, the outlet 66 can simply be inserted directly into the larger portion 78 of the outer cannula 52, such as a circular member inserted through the sidewall of the outer of the larger portion 78.

Figure 4E:
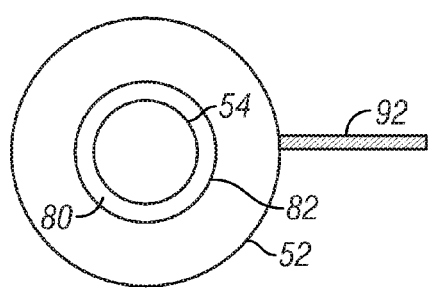
FIG. 4E illustrates a cross sectional schematic of the cannula assembly where the inner cannula is inserted into the outer cannula.

FIG. 4E illustrates a cross sectional schematic of the cannula assembly where the inner cannula is inserted into the outer cannula to form the double wall cannula assembly. The seal 82 engages and seals the opening 80 in the outer cannula 52 with the inner cannula 54 inserted therethrough.

Various basics of the invention have been explained herein. The various techniques and devices disclosed represent a portion of that which those skilled in the art would readily understand from the teachings of this application. Details for the implementation thereof can be added by those with ordinary skill in the art. Such details may be added to the disclosure in another application based on this provisional application and it is believed that the inclusion of such details does not add new subject matter to the application. The accompanying figures may contain additional information not specifically discussed in the text and such information may be described in a later application without adding new subject matter. Additionally, various combinations and permutations of all elements or applications can be created and presented. All can be done to optimize performance in a specific application.

The various steps described herein can be combined with other steps, can occur in a variety of sequences unless otherwise specifically limited, various steps can be interlineated with the stated steps, and the stated steps can be split into multiple steps. Unless the context requires otherwise, the word "comprise" or variations such as "comprises" or "comprising" or the word "includes" and variations, should be understood to imply the inclusion of at least the stated element or step or group of elements or steps or equivalents thereof, and not the exclusion of any other element or step or group of elements or steps or equivalents thereof.

Further, any documents to which reference is made in the application for this patent as well as all references listed in any list of references filed with the application are hereby incorporated by reference. However, to the extent statements might be considered inconsistent with the patenting of this invention such statements are expressly not to be considered as made by the applicant(s).

Also, any directions such as "top," "bottom," "left," "right," "upper," "lower," and other directions and orientations are described herein for clarity in reference to the figures and are not to be limiting of the actual device or system or use of the device or system. The device or system may be used in a number of directions and orientations.

The invention claimed is:

1. A method of withdrawing blood from a heart of a body, the heart having an apex in proximity to a left ventricle and an aortic valve fluidicly disposed between the left ventricle and an aorta, the aorta providing a distribution of blood to the body, comprising:
   a. obtaining a cannula assembly having an outer cannula and an inner cannula, the outer cannula having a transition portion from a first introductory inner perimeter of the outer cannula to a second inner perimeter of the outer cannula, the first introductory inner perimeter being sized in proximity to an outer perimeter of the inner cannula and the second inner perimeter being sized larger than the first introductory inner perimeter, the second inner perimeter forming an annulus around a length of the inner cannula to establish a flow path through the annulus fluidicly separate from a flow path through the inner cannula, the transition portion having a port to allow blood flow into the annulus;
   b. creating an incision in proximity of the apex of the heart;
   c. inserting the cannula assembly through the incision and into the left ventricle of the heart, at least a portion of the outer cannula comprising the transition portion and at least a portion of the annulus being disposed in the left ventricle and fluidicly coupled to the left ventricle;
   d. inserting a portion of the inner cannula through the aortic valve of the heart; and
   e. allowing blood to be withdrawn from the left ventricle into the port and through the annulus to an outlet of the outer cannula to establish a downstream direction in the annulus flow path along the length of the inner cannula disposed inside the outer cannula while restricting blood flow downstream of the transition portion within the heart along the annulus flow path from external to the outer cannula into the annulus, wherein a portion of the outer cannula downstream of the transition portion is disposed within the heart.

2. The method of claim 1, further comprising discharging blood into the aorta through the inner cannula.

3. The method of claim 1, further comprising reducing a contracting pressure of the left ventricle by allowing the blood to be withdrawn.

4. The method of claim 1, wherein inserting the portion of the inner cannula comprises sliding the inner cannula relative to the outer cannula.

5. The method of claim 1, further comprising pumping the blood through a pump and an oxygenator fluidicly coupled between the first cannula and the second cannula.

6. The method of claim 1, further comprising extending an introducer coupled to the inner cannula initially through the aortic valve to reduce a risk of damage to the aortic valve.

7. The method of claim 1, further comprising securing the cannula assembly with a securing plate to the heart.

8. The method of claim 1, wherein creating the incision comprises creating the incision in relative alignment with the aortic valve.

9. A system for withdrawing blood from a heart of a body, the heart having an apex in proximity to a left ventricle and an aortic valve fluidicly disposed between the left ventricle and an aorta, the aorta providing a distribution of blood to the body, the system comprising a cannula assembly comprising:
   a. an inner cannula having an outer perimeter disposed inside an inner perimeter of an outer cannula, and having an introducer adapted to be introduced through the heart apex and extended through the aortic valve; and
   b. an outer cannula disposed around a length of the inner cannula and having a transition portion disposed toward a portion of the cannula assembly adapted to be introduced through an incision in the apex of the heart, the transition portion having an introductory inner perimeter being sized in proximity to an outer perimeter of the inner cannula to reduce blood flow therebetween, the transition portion further having a second inner perimeter larger than the first introductory inner perimeter and distal from the portion to be introduced through the incision, the second inner perimeter of the outer cannula forming an annulus around the inner cannula to establish a flow path through the annulus fluidicly separate from a flow path through the inner cannula, the transition portion of the outer cannula having at least one port to allow blood to be withdrawn from the left ventricle to flow into the port and through the annulus to an outlet of the outer cannula to establish a downstream direction in the annulus flow path, and the outer cannula being further adapted to restrict blood flow downstream of the transition portion within the heart along the annulus flow path from external to the outer cannula into the annulus, wherein a portion of the outer cannula downstream of the transition portion is disposed within the heart.

10. The system of claim 9, further comprising a pump for circulating the blood, a first conduit coupled from an outlet of the outer cannula to the pump, and a second conduit coupled from the pump to the inner cannula.

11. The system of claim 9, further comprising an oxygenator coupled to the pump.

12. The system of claim 9, further comprising a securing plate coupled to the cannula assembly and adapted to secure the cannula assembly to the heart.

13. The system of claim 9, wherein inner cannula is a separate component from the outer cannula and is coupled to the outer cannula through an opening in the outer cannula.

14. A system for withdrawing blood from a body, the system comprising a cannula assembly comprising:
   a. an inner cannula having an outer perimeter disposed inside an inner perimeter of an outer cannula, and having an introducer adapted to be introduced into a blood flow path of the body; and
   b. an outer cannula disposed around a length of the inner cannula and having a transition portion disposed toward a portion of the cannula assembly adapted to be at least partially inserted into the body, the transition portion having an introductory inner perimeter being sized in proximity to an outer perimeter of the inner cannula to reduce blood flow therebetween, the transition portion further having a second inner perimeter sized larger than the first introductory inner perimeter and distal from the portion to be inserted into the body, the second inner perimeter of the outer cannula forming an annulus around the inner cannula to establish a flow path through the annulus fluidicly separate from a flow path through the inner cannula, the transition portion having at least one port to allow blood to be withdrawn from the blood flow path to flow into the port and through the annulus to an outlet of the outer cannula to establish a downstream direction in the annulus flow path, and the outer cannula being further adapted to restrict blood flow downstream of the transition portion within the heart along the annulus flow path from external to the outer cannula into the annulus, wherein a portion of the outer cannula downstream of the transition portion is disposed within the blood flow path.

15. The system of claim 14, wherein the inner cannula is slidably disposed in the outer cannula.

16. The system of claim 14, wherein the inner cannula is coupled to the outer cannula through an opening in the outer cannula and sealed therewith.

17. The system of claim 14, further comprising a pump for circulating the blood, a first conduit coupled from the outlet of the outer cannula to the pump, and a second conduit coupled from the pump to the inner cannula.

18. The system of claim 17, further comprising an oxygenator coupled to the pump.

\* \* \* \* \*